United States Patent
Takata

(10) Patent No.: US 9,755,409 B2
(45) Date of Patent: Sep. 5, 2017

(54) WIRING HARNESS WITH SOUND ABSORBER

(71) Applicants: AutoNetworks Technologies, Ltd., Yokkaichi, Mie (JP); Sumitomo Wiring Systems, Ltd., Yokkaichi, Mie (JP); SUMITOMO ELECTRIC INDUSTRIES, LTD., Osaka-shi, Osaka (JP)

(72) Inventor: Yutaka Takata, Mie (JP)

(73) Assignees: AUTONETWORKS TECHNOLOGIES, LTD. (JP); SUMITOMO WIRING SYSTEMS, LTD. (JP); SUMITOMO ELECTRIC INDUSTRIES, LTD. (JP)

( * ) Notice: Subject to any disclaimer, the term of this patent is extended or adjusted under 35 U.S.C. 154(b) by 0 days.

(21) Appl. No.: 15/116,327

(22) PCT Filed: Jan. 28, 2015

(86) PCT No.: PCT/JP2015/052265
§ 371 (c)(1),
(2) Date: Aug. 3, 2016

(87) PCT Pub. No.: WO2015/125570
PCT Pub. Date: Aug. 27, 2015

(65) Prior Publication Data
US 2017/0012416 A1   Jan. 12, 2017

(30) Foreign Application Priority Data
Feb. 18, 2014 (JP) ................... 2014-028355

(51) Int. Cl.
*H02G 3/04* (2006.01)
*G10K 11/168* (2006.01)
(Continued)

(52) U.S. Cl.
CPC ..... *H02G 3/0406* (2013.01); *A61F 13/00076* (2013.01); *A61F 15/001* (2013.01);
(Continued)

(58) Field of Classification Search
CPC .............. H02G 3/0406; H02G 3/0481; B60R 16/0215; G10K 11/168
(Continued)

(56) References Cited

U.S. PATENT DOCUMENTS

2003/0213608 A1* 11/2003 Tsunoda ............... H02G 11/00
174/72 A
2015/0053479 A1   2/2015 Takata et al.
(Continued)

FOREIGN PATENT DOCUMENTS

JP   2003-201658   7/2003
JP   2003-235126   8/2003
(Continued)

OTHER PUBLICATIONS

International Search Report.

Primary Examiner — Timothy Thompson
Assistant Examiner — Charles Pizzuto
(74) Attorney, Agent, or Firm — Gerald E. Hespos; Michael J. Porco; Matthew T. Hespos

(57) ABSTRACT

Although protective members such as urethane sheets and PVC sheets used for wiring harnesses exhibit very good performance in knocking sound characteristic, they are poor in silencing effect for rubbing sound generated by a wiring harness and a vehicle body or the wiring harness and another member in a vehicle and vehicle interior quietness may be impaired due to the rubbing sound generated in the vehicle. Rubbing sound generated in a vehicle is suppressed by a wiring harness with sound absorber including a sound absorber including a nonwoven fabric having a basis weight (Continued)

of 50 to 400 g/m² and a thickness of 5 to 20 mm and a wiring harness at least partially integrated with the sound absorber.

4 Claims, 5 Drawing Sheets

(51) Int. Cl.
    *B60R 16/02*     (2006.01)
    *B32B 5/02*     (2006.01)
    *B32B 1/08*     (2006.01)
    *B32B 3/02*     (2006.01)
    *A61F 15/00*     (2006.01)
    *A61F 17/00*     (2006.01)
    *A61F 13/00*     (2006.01)

(52) U.S. Cl.
    CPC ............... *A61F 17/00* (2013.01); *B32B 1/08* (2013.01); *B32B 3/02* (2013.01); *B32B 5/022* (2013.01); *B60R 16/0215* (2013.01); *G10K 11/168* (2013.01); *H02G 3/0481* (2013.01); *B32B 2307/102* (2013.01); *B32B 2307/718* (2013.01); *B32B 2605/00* (2013.01)

(58) Field of Classification Search
    USPC ........................................................ 174/72 A
    See application file for complete search history.

(56) References Cited

U.S. PATENT DOCUMENTS

2016/0042730 A1*   2/2016   Takata ................... B32B 5/022
                                                               181/290
2016/0210954 A1*   7/2016   Takata ...................... B32B 5/26

FOREIGN PATENT DOCUMENTS

JP       2006-210228     8/2006
JP       2013-207873     10/2013

* cited by examiner

WIRING HARNESS WITH SOUND ABSORBER

BACKGROUND

1. Field of the Invention

The present invention relates to a wiring harness with sound absorber in which a sound absorber and a wiring harness are integrated.

2. Description of the Related Art

Conventionally, sound insulators and sound absorbers made of soft materials such as glass wool, rock wool, porous ceramic and waste cotton have been provided near devices, which generate noise, in a vehicle for the purpose of enhancing the vehicle interior quietness of an automotive vehicle. However, nonwoven fabrics are used in many of these sound insulators and sound absorbers at present from the perspective of the workability of sound insulators and sound absorbers, influences on human bodies, recyclability, environmental loads and weight reduction.

Further, there have been rapid growths in performances and functions centering on automotive vehicles, electronic products and the like in recent years. For the precise operation of various electronic facilities such as these automotive vehicles and electronic products, it is necessary to use a plurality of wires for internal wiring. These plurality of wires are generally used in the form of a wiring harness. The wiring harness is formed by assembling a plurality of wires into a form necessary for wiring in advance and covering the outer periphery of a wire bundle with a wiring harness protective material having one of various shapes such as a tape shape, a tube shape and a sheet shape after performing necessary branching, the mounting of connectors on ends and the like.

A wiring harness mounted in an automotive vehicle is arranged in the vehicle to electrically connect various electric components including devices which generate noise as described above. This wiring harness may generate noise by contacting a vehicle body or another member or the like in the vehicle such as due to vibration. To suppress such noise, protective materials such as urethane sheets and PVC sheets may be provided in the vehicle. A known wiring harness is shown, for example in Japanese Unexamined Patent Publication No. 2003-235126.

The above protective materials such as urethane sheets or PVC sheets used for the wiring harness have not only a cushioning function, but also a silencing function. Since these have use application and purpose different from those of sound absorbers, they are arranged separately from the sound absorbers in the vehicle.

These protective materials having the silencing function exhibit very good performance in knocking sound characteristic. However, they have a disadvantage of being poor in silencing effect as compared to sound absorbers made of nonwoven fabrics concerning rubbing sound generated by the rubbing of the wiring harness and the vehicle body or the wiring harness and another member in the vehicle. Thus, vehicle interior quietness may be impaired due to the entrance of the rubbing sound generated in the vehicle into the vehicle interior.

SUMMARY

To solve the above problem, a wiring harness with sound absorber according to the present invention includes a sound absorber including a nonwoven fabric having a basis weight of 50 to 400 g/m2 and a thickness of 5 to 20 mm, and a wiring harness at least partially integrated with the sound absorber.

The sound absorber of the wiring harness with sound absorber according to the present invention is excellent in softness and exhibits a high rubbing sound suppressing effect by including the nonwoven fabric having a basis weight of 50 to 400 g/m2 and a thickness of 5 to 20 mm.

Further, since a degree of freedom in the thickness of the sound absorber is enhanced due to the softness thereof, the wiring harness can be flexibly deformed in shape according to a vehicle body and various clearances between members in a vehicle when being arranged in the vehicle. Further, an effect of improving sound absorption performance by filling up the clearances is also expected.

Further, since the sound absorber is integrated with at least a part of the wiring harness, it also has a function as a protective member for the wiring harness and can effectively suppress rubbing sound generated by the contact of the wiring harness and the vehicle body or the wiring harness and another member in the vehicle.

A method for winding or sandwiching the wiring harness with one or a plurality of sound absorbers is considered as a method for integrating the sound absorber(s) and the wiring harness.

Further, a fiber diameter of the nonwoven fabric is preferably 4 to 100 μm to combine sound absorption performance and durability as the sound absorber. This is because the sound absorption performance can be enhanced by reducing the fiber diameter, but the durability of the sound absorber is lost if the fibers are excessively thinned and, conversely, the sound absorption effect of the sound absorber is not exhibited if the fibers are excessively thickened.

According to a wiring harness with sound absorber of the present invention, it is possible to effectively suppress rubbing sound generated by the contact of a wiring harness and a vehicle body or the wiring harness and another member in a vehicle, reduce the entrance of noise into the vehicle interior and enhance vehicle interior quietness.

DETAILED DESCRIPTION

Hereinafter, embodiments of the present invention are described in detail using the drawings.

Figure 1A:
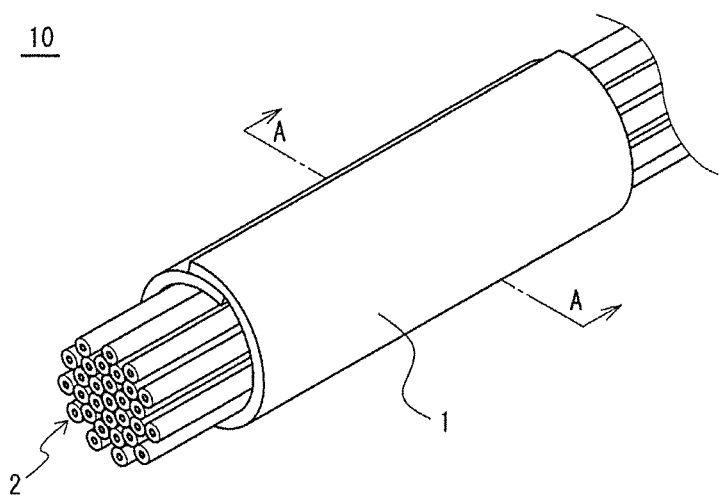
FIG. 1 are an external perspective view and a section of a wiring harness with sound absorber including one sound absorber.
Figure 1B:
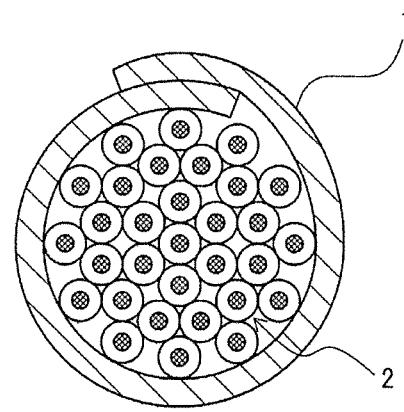

FIG. 1 are an external perspective view and a section of a wiring harness with sound absorber including one sound absorber, wherein FIG. 1(a) is the external perspective view of a wiring harness with sound absorber 10 and FIG. 1(b) is a section along A-A of FIG. 1(a).

The wiring harness with sound absorber 10 is formed by winding one sound absorber 1 around a wiring harness 2 composed of a wire bundle formed by bundling a plurality of wires each configured such that a core is covered around with an insulator. The wiring harness 2 is not limited to the wire bundle and may be composed of a single wire.

A basis weight and a thickness of the sound absorber 1 are within a range of 50 to 400 g/m$^2$ and a range of 5 to 20 mm. More preferably, the basis weight is within a range of 200 to 300 g/m$^2$ and the thickness is within a range of 10 to 15 mm. This is to combine the softness of the sound absorber 1 and a rubbing sound suppressing effect.

The basis weight and thickness of the sound absorber 1 need not be uniform in the entirety of the sound absorber 1 and may differ if they are within the range of 50 to 400 g/m2 and the range of 5 to 20 mm.

Needle punching, thermal bonding, chemical bonding and the like can be used as a production method of the sound absorber 1.

Besides polyesters such as polyethylene terephthalate and polybutylene terephthalate, polyolefin, nylon, polyamide, polyvinyl chloride, rayon, acrylonitrile, cellulose, kenaf, glass and the like can be used as fibers constituting the sound absorber 1.

A cross-sectional shape of the above fibers is not particularly limited and fibers of a core-sheath type, a cylindrical type, a hollow type and a side-by-side type and fibers having a modified cross-section different in shape from normal fibers may be used.

A fiber diameter of the above fibers is preferably within a range of 4 to 100 µm. This is to combine the sound absorption performance and the durability of the sound absorber 1.

The softness of the sound absorber 1 is preferably such that a vertical drag when two overlapping nonwoven fabrics of the sound absorber 1 having a diameter ϕ of 60 mm are compressed by a cylindrical plate having a diameter ϕ of 60 mm and a compression rate reaches 50% is less than 10 N, more preferably less than 5N.

The wiring harness with sound absorber 10 is formed by integrating the sound absorber 1 and the wiring harness 2. Thus, the wiring harness 2 can be arranged by flexibly deforming the sound absorber 1 in shape according to a vehicle body and various clearances between members in a vehicle, rubbing sound generated by the contact of the wiring harness 2 with the vehicle body or another member in the vehicle such as due to vibration generated during the travel of the vehicle can be effectively suppressed, and the sound absorber 1 functions also as a protective material for the wiring harness 2. Further, an effect of improving sound absorption performance by filling up the clearances is also expected.

An example of a means for fixing and integrating the sound absorber 1 to and with the wiring harness 2 is a method for bonding the sound absorber 1 using an adhesive, a stapler or the like. Besides, the sound absorber 1 may be fixed using an unillustrated separate mounting member.

Figure 2A:
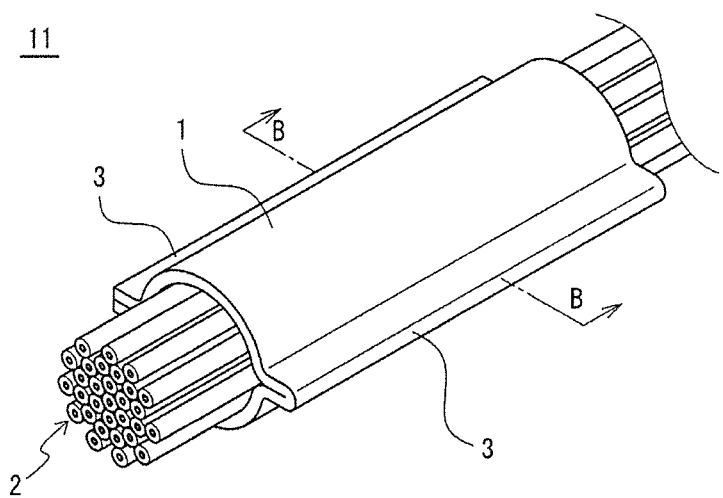
FIG. 2 are an external perspective view and a section of another form of a wiring harness with sound absorber including one sound absorber.
Figure 2B:
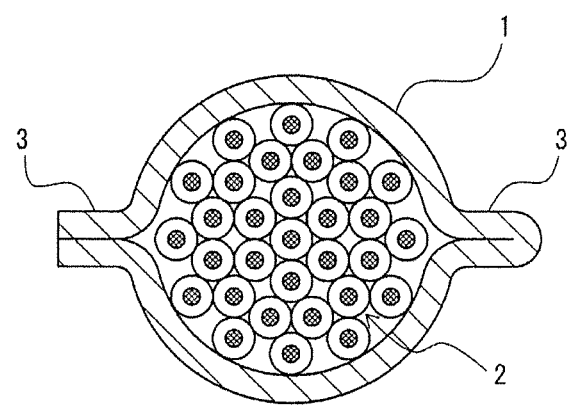

FIG. 2 are an external perspective view and a section of another embodiment of a wiring harness with sound absorber including one sound absorber, wherein FIG. 2(a) is the external perspective view of a wiring harness with sound absorber 11 and FIG. 2(b) is a section along B-B of FIG. 2(a).

The wiring harness with sound absorber 11 is the same as the wiring harness with sound absorber 10 in that one sound absorber 1 is wound on the outer periphery of a wiring harness 2, but the sound absorber 1 wound in the wiring harness with sound absorber 11 is formed with two ear portions 3 extending along an axial direction thereof and extending radially outward from circumferentially symmetrical positions. The ear portions 3 are formed by bonding circumferential surplus parts of the sound absorber 1 using an adhesive, a stapler or the like, one of the ear portions 3 is formed by bonding circumferential end parts of the sound absorber 1 and the other is formed by bending and bonding the surplus part at the position symmetrical with the one ear portion 3. Since the sound absorber 1 includes the ear portions 3, it is possible to fill up larger clearances in the vehicle and improve sound absorption performance.

Figure 3A:
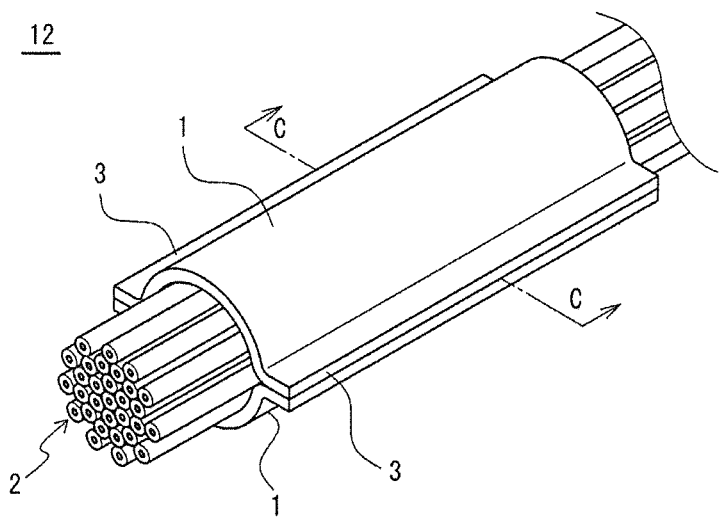
FIG. 3 are an external perspective view and a section of a wiring harness with sound absorber sandwiched between two sound absorbers.
Figure 3B:
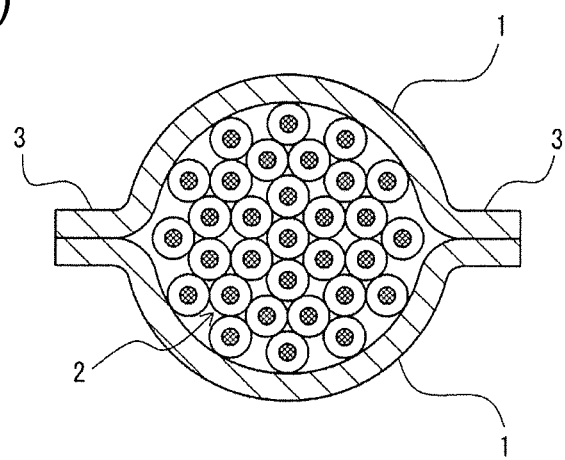

FIG. 3 are an external perspective view and a section of another embodiment of a wiring harness with sound absorber sandwiched between two sound absorbers, wherein FIG. 3(a) is the external perspective view of a wiring harness with sound absorber 12 and FIG. 3(b) is a section along C-C of FIG. 3(a).

The wiring harness with sound absorber 12 has the same configuration and effects as the wiring harness with sound absorber 11 except in that a sound absorber covering a wiring harness 2 is composed of two sound absorbers 1. Such two sound absorbers 1 need not have the same basis weight and thickness and may differ if they are within a range of 50 to 400 g/m$^2$ and a range of 5 to 20 mm.

EXAMPLES

Examples and Comparative Examples of the sound absorber according to the wiring harness with sound absorber of the present invention are described below. Two overlapping nonwoven fabrics produced by needle punching were used as the sound absorber of each of these Examples and Comparative Examples. Further, polyester fibers were used for the nonwoven fabrics of the sound absorbers and a fiber diameter was 14 µm.

A basis weight and a thickness of the sound absorber of each of Examples and Comparative Examples were: a basis weight of 50 g/m2 and a thickness of 5 mm in Example 1, a basis weight of 200 g/m2 and a thickness of 10 mm in Example 2, a basis weight of 300 g/m2 and a thickness of 15 mm in Example 3, a basis weight of 400 g/m2 and a thickness of 20 mm in Example 4, a basis weight of 10 g/m2 and a thickness of 2 mm in Comparative Example 1 and a basis weight of 500 g/m2 and a thickness of 25 mm in Comparative Example 2.

[Softness Measurement]

Figure 4:
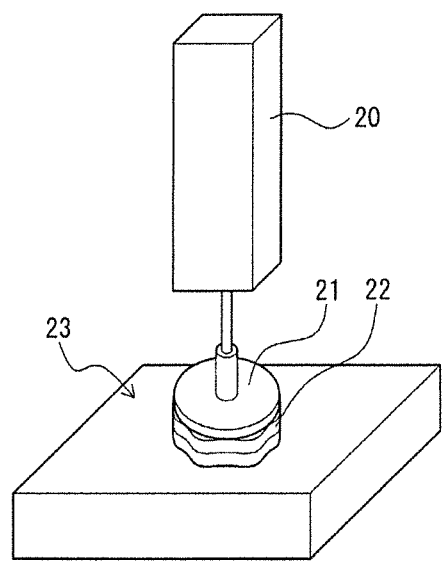
FIG. 4 is a diagram showing a method for measuring the softness of the sound absorber.

A softness measurement was conducted by a method of FIG. 4 for the sound absorbers of Examples 1 to 4 and Comparative Examples 1, 2. The detailed measurement method is described below.

A pressing plate 21, which is a cylindrical plate having a diameter ϕ of 60 mm, was attached to a force gauge 20 and a vertical drag when a sound absorber 23 was compressed by the pressing plate 21 was measured. A compression speed was set at 1 mm/min and a value of the force gauge 20 was obtained when a compression rate became 50% with respect to a thickness of the sound absorber 23 formed by overlapping two nonwoven fabrics 22 having a diameter ϕ of 60 mm equal to that of the pressing plate 21. The sound absorber 23 was determined to be good "○", assuming that it has sufficient softness to obtain effects expected for the sound absorber of the present invention, when the value measured by this method was less than 10 N while being determined to be bad "x" when the value is not less than 10 N. That result is shown in Table 1.

As shown in Table 1, a softness of less than 10 N is maintained in the sound absorbers whose basis weights are from 50 g/m2 to 400 g/m2 and whose thicknesses are 5 mm to 20 mm (Examples 1 to 4, Comparative Example 1). Particularly, the softness of the sound absorber is less than 5 N when the basis weight is not more than 300 g/m2 and the thickness is not larger than 15 mm (Examples 1 to 3, Comparative Example 1). In the sound absorber having a basis weight of 500 g/m2 and a thickness of 25 mm (Comparative Example 2), the vertical drag increases to 21.5 N and softness is drastically lost.

[Rubbing Sound Measurement]

In accordance with SAE J2192 "Recommended Testing Methods for Physical Protection of Wiring Harnesses", rubbing sound suppressing performance was evaluated for each of the sound absorbers of Examples 1 to 4 and Comparative Examples 1, 2. Dimensions of each of the sound absorbers of Examples and Comparative Examples were 200 mm×50 mm. A measurement condition of a noise meter was 3 seconds in LAmax and a calculated overall value (O.A. value) was compared in the form of a numerical value. Further, a sound insulation box was installed so as not to pick up surrounding noise and a measurement was conducted in the sound insulation box.

Figure 5A:
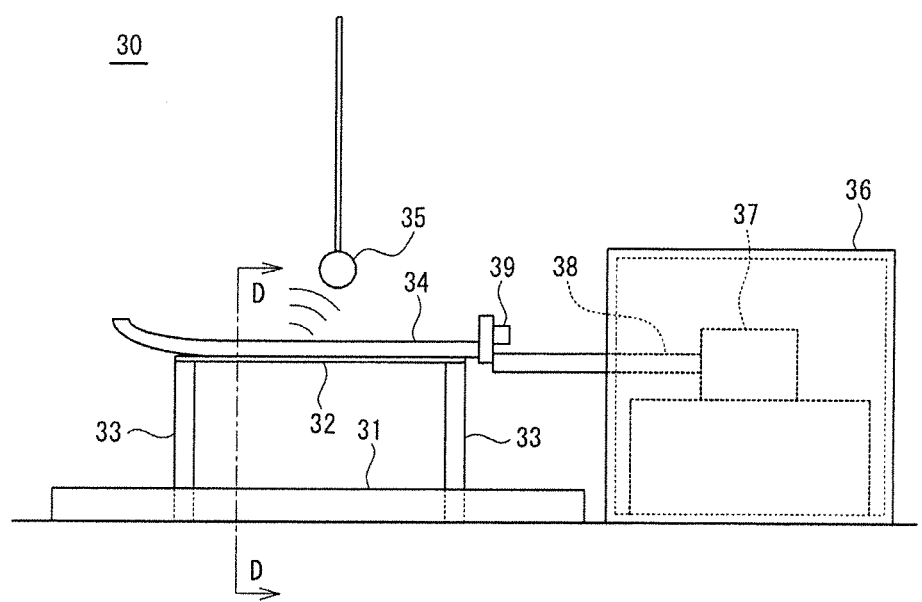
FIG. 5 are diagrams showing a method for measuring rubbing sound of the sound absorber.
Figure 5B:
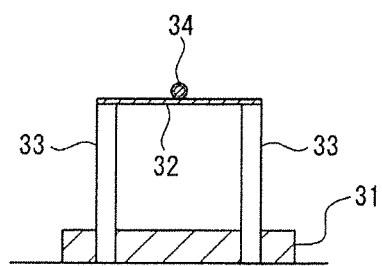

FIG. 5(a) is a diagram showing a specific method for measuring rubbing sound and FIG. 5(b) is a section along D-D of FIG. 5(a). That measurement method is described in detail below.

A sound absorber 31 (sound absorber different from the sound absorber in the present invention) is stuck to an inner wall of a sound insulation box 30 and an iron plate 32 having a thickness of 1.6 mm and an area of 300 mm×500 mm is arranged on a floor part in the sound insulation box 30 while having four corners thereof supported by leg portions 33. A test piece 34 formed by integrating the sound absorber of Examples 1 to 4 and Comparative Examples 1, 2 and a wiring harness and having a diameter φ of 15 mm is placed on the upper surface of the iron plate 32 to extend along a longitudinal direction of the iron plate 32 in a center with respect to a lateral direction. A microphone 35 for collecting rubbing sound is arranged at a position spaced upwardly from the iron plate 32 by 150 mm. A tool 38 extending from an exciter 37 abated with a soundproof material 36 is coupled to one end part of the test piece 34 and an acceleration sensor 39 is attached to this end part.

Under such an environment, the test piece 34 was excited at both amplitudes of 5 mm and 9 Hz in an axial direction by the exciter 37. Dark noise was measured at 26 dB and the rubbing sound generated by the test piece 34 was determined be good "○" if it was lower than 38 dB, which was rubbing sound generated by a urethane sheet protective member of "Eptsealer" No. 685 produced by Nitto Denko Cooperation while being determined to be bad "x" if it was not lower than 38 dB. That result is shown in Table 1.

As shown in Table 1, rubbing sound of lower than 38 dB is maintained in the sound absorbers whose basis weights are from 50 g/m2 to 500 g/m2 and whose thicknesses are 5 mm to 25 mm (Examples 1 to 4, Comparative Example 2). Particularly, the rubbing sound of the sound absorber when the basis weight is not less than 200 g/m2 and the thickness is not smaller than 10 mm (Examples 2 to 4, Comparative Example 2) is lower than 30 dB. In the sound absorber thinner and coarser than Example 1 (Comparative Example 1), the rubbing sound is drastically increased to 45.8 dB.

TABLE 1

|  | Ex. 1 | Ex. 2 | Ex. 3 | Ex. 4 | C-Ex. 1 | C-Ex. 2 |
|---|---|---|---|---|---|---|
| Basis Weight (g/m$^2$) | 50 | 200 | 300 | 400 | 10 | 500 |
| Thickness (mm) | 5 | 10 | 15 | 20 | 2 | 25 |
| Softness (N) | 2.1 | 3.4 | 4.5 | 8.8 | 1.8 | 21.5 |
| Softness Determination | ○ | ○ | ○ | ○ | ○ | x |
| Rubbing Sound dB | 30.3 | 26.8 | 25.5 | 26.3 | 45.8 | 25.9 |
| Rubbing Sound Determination | ○ | ○ | ○ | ○ | x | ○ |

By integrating the above results of [Softness Measurement] and [Rubbing Sound Measurement] for Examples 1 to 4 and Comparative Examples 1, 2, it is found that the softness of the sound absorber and the rubbing sound suppressing effect can be combined by setting the basis weight and the thickness of the nonwoven fabrics constituting the sound absorber within the range of 50 to 400 g/m$^2$ and the range of 5 to 20 mm. Particularly, the effect of combination is notable within a basis weight range of 200 to 300 g/m$^2$ and a thickness range of 10 to 15 mm.

Although Examples and Comparative Examples of the present invention have been described in detail above, the present invention is not limited to the above Examples at all and various changes can be made without departing from the gist of the present invention.

The invention claimed is:

1. A wiring harness with sound absorber, comprising:
   a sound absorber including a nonwoven fabric having a basis weight of 50 to 400 g/m$^2$ and a thickness of 5 to 20 mm; and
   a wiring harness at least partially integrated with the sound absorber,
   a vertical drag of the sound absorber when a compression rate in a thickness direction becomes 50% being smaller than 10 N.

2. The wiring harness with sound absorber of claim 1, wherein the sound absorber and the wiring harness are integrated by sandwiching at least a part of the wiring harness by one or a plurality of the sound absorbers.

3. The wiring harness with sound absorber of claim 2, wherein a fiber diameter of the nonwoven fabric is 4 to 100μm.

4. The wiring harness with sound absorber of claim 1, wherein a fiber diameter of the nonwoven fabric is 4 to 100μm.

* * * * *